United States Patent
Finlayson et al.

(10) Patent No.: US 10,857,040 B2
(45) Date of Patent: Dec. 8, 2020

(54) DISPOSABLE ABSORBENT GARMENT HAVING ELASTIC SHEET MATERIAL AND ELASTIC STRANDS

(71) Applicant: Attends Healthcare Products, Inc., Greenville, SC (US)

(72) Inventors: Richard E. Finlayson, Raleigh, NC (US); William W. Gaston, Greenville, NC (US)

(73) Assignee: ATTENDS HEALTHCARE PRODUCTS, INC., Greenville, SC (US)

(*) Notice: Subject to any disclaimer, the term of this patent is extended or adjusted under 35 U.S.C. 154(b) by 1154 days.

(21) Appl. No.: 14/966,898

(22) Filed: Dec. 11, 2015

(65) Prior Publication Data

US 2016/0166444 A1    Jun. 16, 2016

Related U.S. Application Data

(60) Provisional application No. 62/090,503, filed on Dec. 11, 2014.

(51) Int. Cl.
*A61F 13/49*      (2006.01)
*A61F 13/496*     (2006.01)

(52) U.S. Cl.
CPC ...... *A61F 13/49012* (2013.01); *A61F 13/496* (2013.01); *A61F 13/49017* (2013.01);
(Continued)

(58) Field of Classification Search
CPC .......... A61F 13/49012; A61F 13/49017; A61F 13/496; A61F 2013/49087; A61F 2013/49092; A61F 13/49019; A61F 13/4902; A61F 13/4906; A61F 13/49061; A61F 13/49011
See application file for complete search history.

(56) References Cited

U.S. PATENT DOCUMENTS 5,422,172 A    6/1995  Wu ............................ 442/62
5,567,501 A   10/1996  Srinivasan et al. ......... 428/137
(Continued)

FOREIGN PATENT DOCUMENTS

EP          0685586        12/1995
WO     WO 2001/045613      6/2001
(Continued)

*Primary Examiner* — Michele M Kidwell
(74) *Attorney, Agent, or Firm* — Norton Rose Fulbright US LLP

(57) ABSTRACT

Disposable absorbent garments, comprising front and rear waist and a central absorbent assembly comprising a liquid-absorbent core, where at least one of the front and rear waist portions comprises: a composite of an elastic sheet material and a non-woven fabric layer, and a plurality of elastic strands. In some of the present garments, the elastic strands are positioned on both sides of the liquid-absorbent core, and each strand has a first end laterally offset from the liquid-absorbent core and extending outward toward a respective leg edge of the waist portion. In others of the present garments, the elastic strands are positioned between the absorbent core and the elastic sheet material, and each extends laterally a majority of the distance between first and second side edges.

19 Claims, 4 Drawing Sheets

(52) U.S. Cl.
CPC .............. *A61F 2013/49087* (2013.01); *A61F 2013/49092* (2013.01)

(56) References Cited

U.S. PATENT DOCUMENTS

| | | | |
|---|---|---|---|
| 5,745,922 A | 5/1998 | Rajala et al. | 2/243.1 |
| 5,851,935 A | 12/1998 | Srinivasan et al. | 442/328 |
| 5,882,769 A | 3/1999 | McCormack et al. | 428/152 |
| 6,049,916 A | 4/2000 | Rajala et al. | 2/400 |
| 6,098,203 A | 8/2000 | Rajala et al. | 2/401 |
| 6,217,690 B1 | 4/2001 | Rajala et al. | 156/161 |
| 6,260,211 B1 | 7/2001 | Rajala et al. | 2/401 |
| 6,375,646 B1 | 4/2002 | Widlund et al. | 604/385.3 |
| 6,461,457 B1 | 10/2002 | Taylor et al. | 156/73.1 |
| 6,472,084 B1 | 10/2002 | Middlesworth et al. | 428/517 |
| 6,554,815 B1 | 4/2003 | Umebayashi | 604/385.27 |
| 6,572,595 B1 | 6/2003 | Klemp et al. | 604/385.01 |
| 6,808,791 B2 | 10/2004 | Curro et al. | 428/198 |
| 6,830,800 B2 | 12/2004 | Curro et al. | 428/136 |
| 6,863,960 B2 | 3/2005 | Curro et al. | 428/198 |
| 6,878,433 B2 | 4/2005 | Curro et al. | 428/198 |
| 6,884,494 B1 | 4/2005 | Curro et al. | 428/196 |
| 6,923,797 B2 | 8/2005 | Shinohara et al. | 604/385.27 |
| 6,974,514 B2 | 12/2005 | Hamulski et al. | 156/73.1 |
| 6,986,932 B2 | 1/2006 | Zink et al. | 428/138 |
| 6,994,761 B2 | 2/2006 | Klemp et al. | 156/73.3 |
| 7,000,260 B2 | 2/2006 | Rajala et al. | 2/400 |
| 7,037,569 B2 | 5/2006 | Curro et al. | 428/138 |
| 7,083,691 B2 | 8/2006 | Hamulski et al. | 156/73.1 |
| 7,087,289 B2 | 8/2006 | Soon et al. | 428/137 |
| 7,449,014 B2 * | 11/2008 | Oba | A61F 13/49017 604/385.01 |
| 7,604,624 B2 | 10/2009 | Veith et al. | 604/385.22 |
| 7,749,211 B2 | 7/2010 | Van Gompel et al. | 604/385.27 |
| 7,771,407 B2 | 8/2010 | Umebayashi | 604/385.22 |
| 7,803,244 B2 | 9/2010 | Siqueira et al. | 156/229 |
| 7,993,320 B2 | 8/2011 | Hornung et al. | 604/385.3 |
| 8,016,806 B2 | 9/2011 | Hornung et al. | 604/385.3 |
| 8,025,652 B2 | 9/2011 | Hornung et al. | 604/385.3 |
| 8,038,662 B2 | 10/2011 | Hornung et al. | 604/385.3 |
| 8,142,590 B2 | 3/2012 | Rajala et al. | 156/226 |
| 8,147,476 B2 | 4/2012 | Veith et al. | 604/385.24 |
| 8,622,984 B2 | 1/2014 | Rajala et al. | 604/385.27 |
| 8,664,469 B2 | 3/2014 | Veith et al. | 604/367 |
| 2004/0127868 A1 * | 7/2004 | Olson | A61F 13/49017 604/367 |
| 2005/0075618 A1 * | 4/2005 | Kenmochi | A61F 13/49001 604/385.27 |
| 2005/0215964 A1 | 9/2005 | Autran et al. | 604/358 |
| 2006/0169387 A1 | 8/2006 | Nayar et al. | 156/73.1 |
| 2007/0298262 A1 | 12/2007 | Quiram et al. | 428/212 |
| 2008/0000003 A1 | 1/2008 | Melander | 2/69 |
| 2008/0033387 A1 | 2/2008 | Wastlund-Karlsson et al. | 604/385.23 |
| 2008/0045917 A1 | 2/2008 | Autran et al. | 604/385.22 |
| 2008/0319130 A1 | 12/2008 | Chang | 525/88 |
| 2009/0143757 A1 * | 6/2009 | Hornung | A61F 13/496 604/385.29 |
| 2009/0299314 A1 | 12/2009 | Middlesworth et al. | 604/367 |
| 2012/0095429 A1 * | 4/2012 | Kobayashi | A61F 13/15804 604/385.16 |
| 2012/0328845 A1 | 12/2012 | Middlesworth et al. | 428/174 |
| 2013/0060219 A1 * | 3/2013 | Mukai | A61F 13/49058 604/385.3 |
| 2014/0128830 A1 | 5/2014 | Veith et al. | 604/385.16 |
| 2014/0148776 A1 * | 5/2014 | Gassner | A61F 13/49011 604/385.24 |
| 2015/0148768 A1 * | 5/2015 | Fukasawa | A61F 13/49466 604/385.16 |

FOREIGN PATENT DOCUMENTS

| | | |
|---|---|---|
| WO | WO 2007/133146 | 11/2007 |
| WO | WO 2010/050867 | 5/2010 |

* cited by examiner

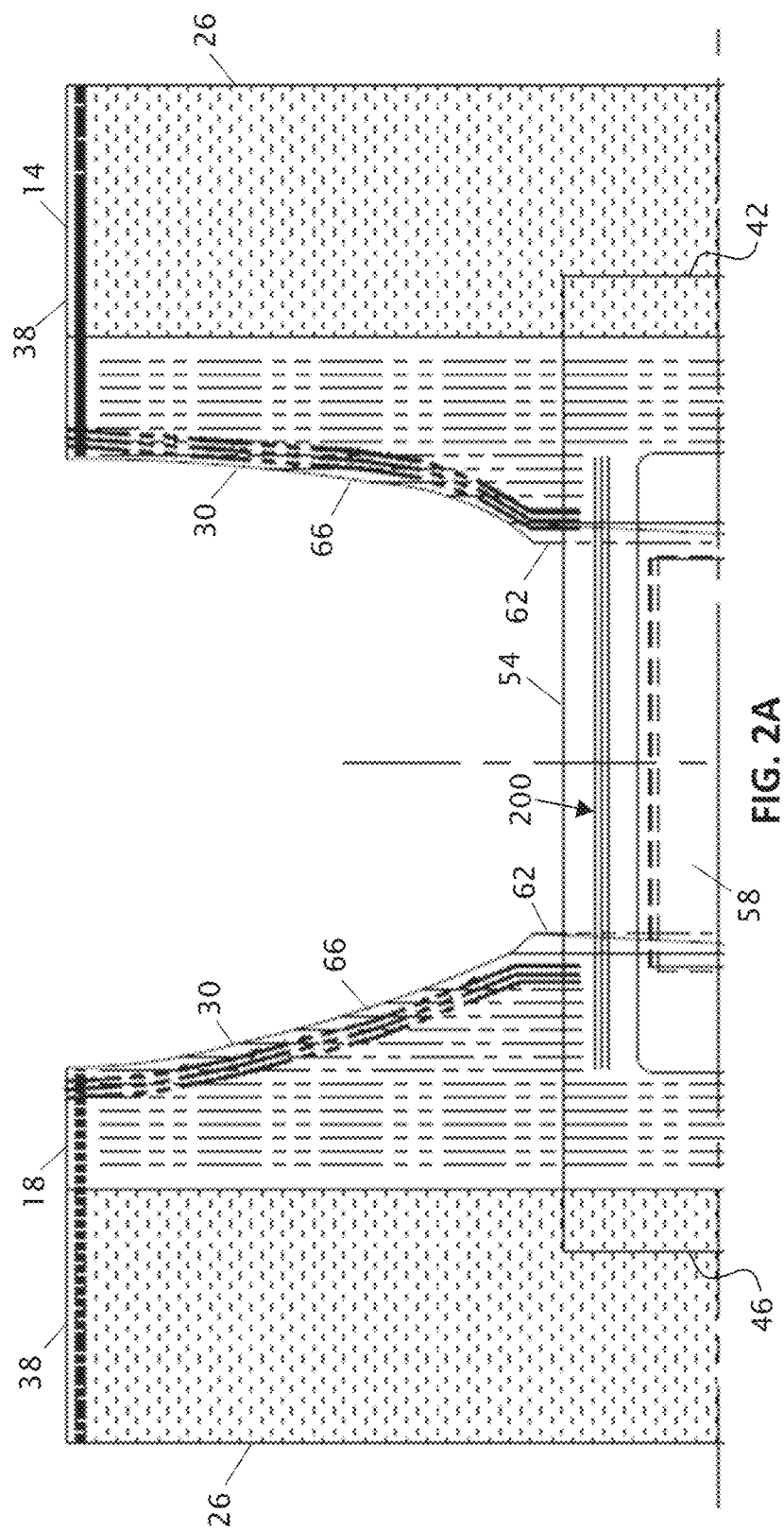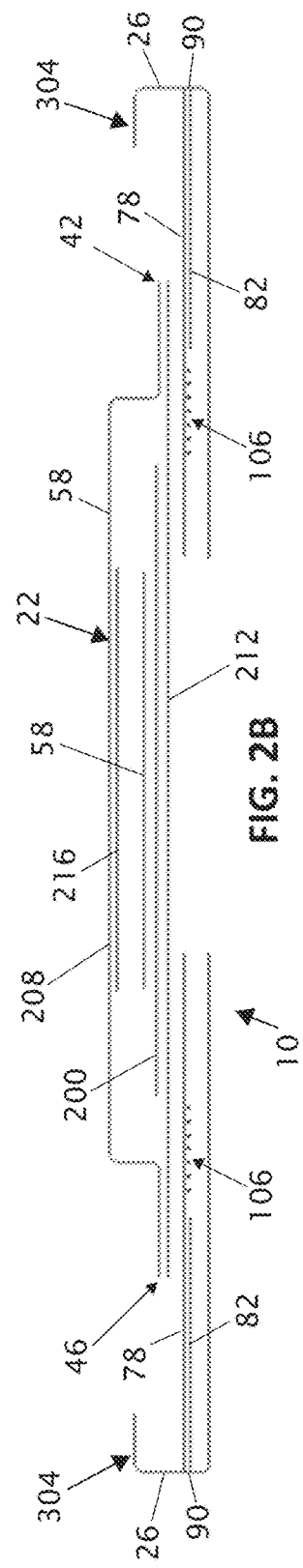

DISPOSABLE ABSORBENT GARMENT HAVING ELASTIC SHEET MATERIAL AND ELASTIC STRANDS

CROSS REFERENCE TO RELATED APPLICATION

This application claims priority to U.S. Provisional Patent Application No. 62/090,503, filed Dec. 11, 2014, which is incorporated by reference in its entirety.

FIELD OF INVENTION

The present invention relates generally to disposable absorbent garments, such as, for example, for adult incontinence use or infant care; and, more particularly, but not by of limitation, to brief-like disposable absorbent products including at least one waist portion that includes a combination of elastic sheet material and elastic strand material for improved comfort and containment characteristics.

BACKGROUND

Disposable absorbent products, including diapers, training pants, adult incontinence briefs, and the like, have found widespread acceptance in the marketplace in view of the effective comfort and containment characteristics they provide for wearers. Improvements in the use of elasticized materials, breathable materials, and suitably liquid-impermeable materials have enhanced performance and comfort of these products. The use of so-called superabsorbent polymers (SAP), typically in combination with absorbent hydrophilic fibers such a comminuted wood pulp, have permitted these types of products to be relatively thin and comfortable for wearers, while still providing the desired containment characteristics.

Disposable absorbent products of this nature are typically provided with elasticized regions, such as at the leg and waist openings, to enhanced fit and containment. Elastication is generally provided by incorporating elastic strand materials or elastic film materials, typically in combination with suitable nonwoven fabrics from which the products are formed.

SUMMARY

The present embodiments include improved disposable absorbent garments that can be provided with a brief-like configuration, wherein at least one (e.g., both) of the waist portions of the garment includes a combination or hybrid of elastic sheet and elastic strand materials for improved fit and comfort for a wearer. For example, the elastic sheet and elastic strand materials acte in combination with the associated absorbent structure to provide improved fit and containment characteristics.

At least some of the present a disposable absorbent products can include front and rear waist portions at least partially (e.g., in combination with a central absorbent assembly or crotch portion) defining brief-like configuration with leg and waist openings. Such products can be provided with tearable side seams by which the front and rear waist portions are joined to each other to at least partially define the waist and leg openings. In some of the present garments, each of the front and rear waist portions include a combination of elastic sheet and elastic strand materials, which promote efficient manufacture, and secure and comfortable fit by a wearer, while providing the desired containment characteristic.

The hybrid nature of the present film-and-strand elastic structure has been found to provide important improvements in performance and ease of use. For example, the elastic structure promotes ease of product removal, which can be particularly important for users with limited mobility. The structure has also been found to desirably provide improved openness and "airiness" at the leg openings, while still maintaining the desired containment characteristics. Chafing and other soreness or irritations at the legs are desirably reduced, since tight elastic elements at the leg openings are avoided. Enhanced garment positioning and fit are achieved by the construction, with a lighter weight garment with improved breathability being provided.

Some embodiments of the present disposable absorbent garments comprise: front and rear waist portions each having a waist edge, a leg edge, and first and second side edges extending between the waist edge and the leg edge; and a central absorbent assembly having a first end, a second end, and first and second leg edges extending between the first and second ends, the central absorbent assembly coupled to the front and rear waist portions such that the central absorbent assembly extends between the respective leg edges of the front and rear waist portions, the central absorbent assembly comprising a liquid-permeable facing layer, a substantially liquid-impermeable backing layer, and a liquid-absorbent core positioned between the facing layer and the backing layer. In such embodiments, at least one of the front and rear waist portions comprises: a composite of an elastic sheet material and a non-woven fabric layer, the elastic sheet material overlapping a respective end of the central absorbent assembly and extending toward the waist edge of the waist portion; and a first plurality of elastic strands on both sides of the liquid-absorbent core, each of the first plurality of elastic strands having a first end laterally offset from the liquid-absorbent core and extending outward toward a respective leg edge of the waist portion.

In some embodiments of the present disposable absorbent garments, the at least one of the front and rear waist portions further comprises: a second plurality of elastic strands between the absorbent core and the elastic sheet material, each of the second plurality of elastic strands extending laterally across a majority of the waist portion between the first and second side edges.

In some embodiments of the present disposable absorbent garments, the at least one of the first and second waist portions further comprises: a third plurality of elastic strands each having a first end laterally offset from the liquid-absorbent core and extending outward along a respective leg edge and toward a respective side edge of the waist portion. In some embodiments, the first end of each of the third plurality of elastic strands overlaps a portion of the central absorbent assembly.

In some embodiments of the present disposable absorbent garments, the first end of each of the first plurality of elastic strands overlaps a portion of the central absorbent assembly. In some embodiments, the central absorbent assembly further comprises: a first leg elastic element extending parallel to a portion of the first leg edge between the first leg edge and the liquid-absorbent core; and a second leg elastic element extending parallel to a portion of the second leg edge between the second leg edge and the liquid-absorbent core. In some embodiments, the first leg elastic element is disposed between a first portion of the first plurality of elastic strands and the liquid-absorbent core, and the second elastic leg element is disposed between a second portion of the first plurality of elastic strands and the liquid-absorbent core. In some embodiments, the first leg elastic element comprises a plurality of elastic strands, and the second leg elastic element comprises a plurality of elastic strands.

In some embodiments of the present disposable absorbent garments, the central absorbent assembly further comprises: a liquid-acquisition layer positioned between the facing layer and the liquid-absorbent core. In some embodiments, the central absorbent assembly further comprises: a liquid-absorbent surge layer positioned between the acquisition layer and the liquid-absorbent core, the liquid-absorbent surge layer configured to receive liquid that passes through the facing layer and the acquisition layer, and transfer the received liquid into the liquid absorbent core.

In some embodiments of the present disposable absorbent garments, the first side edge of the front waist portion is coupled to the first side edge of the rear waist portion, and the second side edge of the front waist portion is coupled to the second side edge of the rear waist portion, such that the central absorbent assembly and the front and rear waist portions together define a pair of leg openings each configured to receive a leg of a wearer. In some embodiments, the first side edge of the front waist portion is coupled to the first side edge of the rear waist portion at a first tearable side seam, and the second side edge of the front portion is coupled to the second side edge of the rear waist portion at a second tearable side seam. In some embodiments, the first and second tearable side seams are configured to facilitate removal of the garment from a wearer by detaching the respective first side edges of the front and rear waist portions, the respective second side edges of the front and rear waist portions, or the first and second side edges of the front and rear waist portions.

In some embodiments of the present disposable absorbent garments, in the at least one of the front and rear waist portions, the elastic sheet material extends to the waist edge of the waist portion.

In some embodiments of the present disposable absorbent garments, the at least one of the front and rear waist portions comprises a plurality of waist elastic elements positioned between the waist edge and the elastic sheet material. In some embodiments, the plurality of waist elastic elements are positioned within an overturned portion of the non-woven fabric layer.

In some embodiments of the present disposable absorbent garments, the front waist portion is substantially similar to the rear waist portion.

Some embodiments of the present disposable absorbent garments comprise: front and rear waist portions each having a waist edge, a leg edge, and first and second side edges extending between the waist edge and the leg edge; and a central absorbent assembly having a first end, a second end, and first and second leg edges extending between the first and second ends, the central absorbent assembly coupled to the front and rear waist portions such that the central absorbent assembly extends between the respective leg edges of the front and rear waist portions, the central absorbent assembly comprising a liquid-permeable facing layer, a substantially liquid-impermeable backing layer, and a liquid-absorbent core positioned between the facing layer and the backing layer; where at least one of the front and rear waist portions comprises: a composite of an elastic sheet material and a non-woven fabric layer, the elastic sheet material overlapping a respective end of the central absorbent assembly and extending toward the waist edge of the waist portion; and a first plurality of elastic strands between the absorbent core and the elastic sheet material, each of the second plurality of elastic strands extending laterally a majority of the distance between the first and second side edges. In some such embodiments, the first side edge of the front waist portion is coupled to the first side edge of the rear waist portion at a first tearable side seam, and the second side edge of the front portion is coupled to the second side edge of the rear waist portion at a second tearable side seam. In some such embodiments, the first plurality of elastic strands do not overlap the tearable side seams.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "absorbent article" and "absorbent garment" are used in this disclosure to refer to garments or articles that are configured to absorb and contain exudates and, more specifically, refer to garments or articles that are placed against or in proximity to the body of a wearer to absorb and contain the exudates discharged from the wearer's body. Examples of such absorbent articles or absorbent garments include diapers, training pants, feminine hygiene products, bibs, wound dressing, bed pads, and adult incontinence products. The term "disposable" when used with "absorbent article" or "absorbent garment" refers to garments and articles that are intended to be discarded after a single use.

"Absorbent core" is used in this disclosure to refer to a structure positioned between a topsheet and backsheet of an absorbent article for absorbing and containing liquid received by the absorbent article. An absorbent core can comprise one or more substrates, absorbent polymer material, adhesives, and/or other materials to bind absorbent materials in the absorbent core.

A device or system that is configured in a certain way is configured in at least that way, but it can also be configured in other ways than those specifically described.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIG. 2A depicts an enlarged, cutaway plan view of the left half of the garment of FIG. 1.

FIG. 2B depicts an enlarged, cross-sectional view of the garment of FIG. 1.

DETAILED DESCRIPTION OF ILLUSTRATIVE EMBODIMENTS

Figure 1:
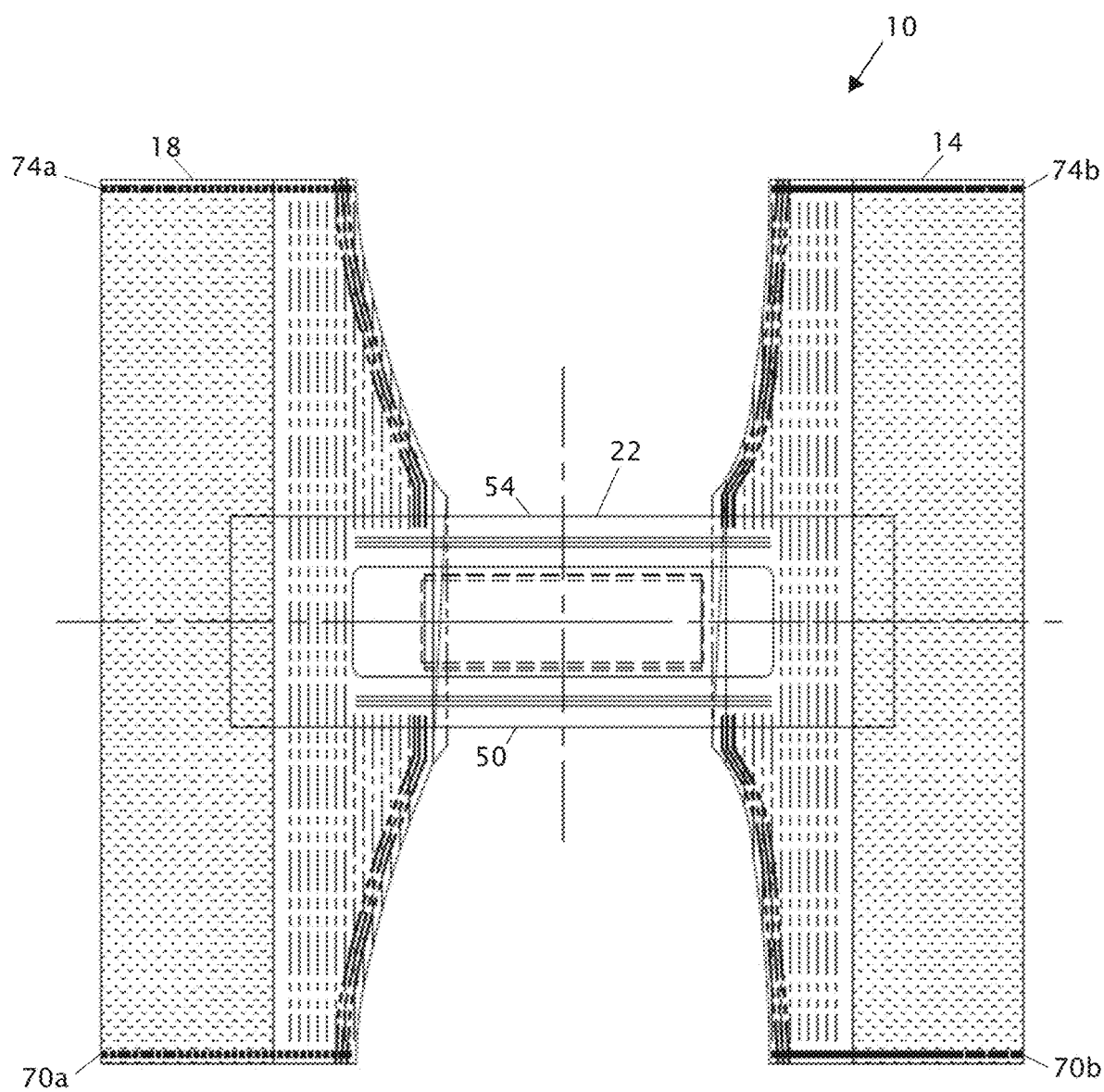
FIG. 1 depicts a diagrammatic, top plan view of one example of the present disposable absorbent garments.
Figure 3A:
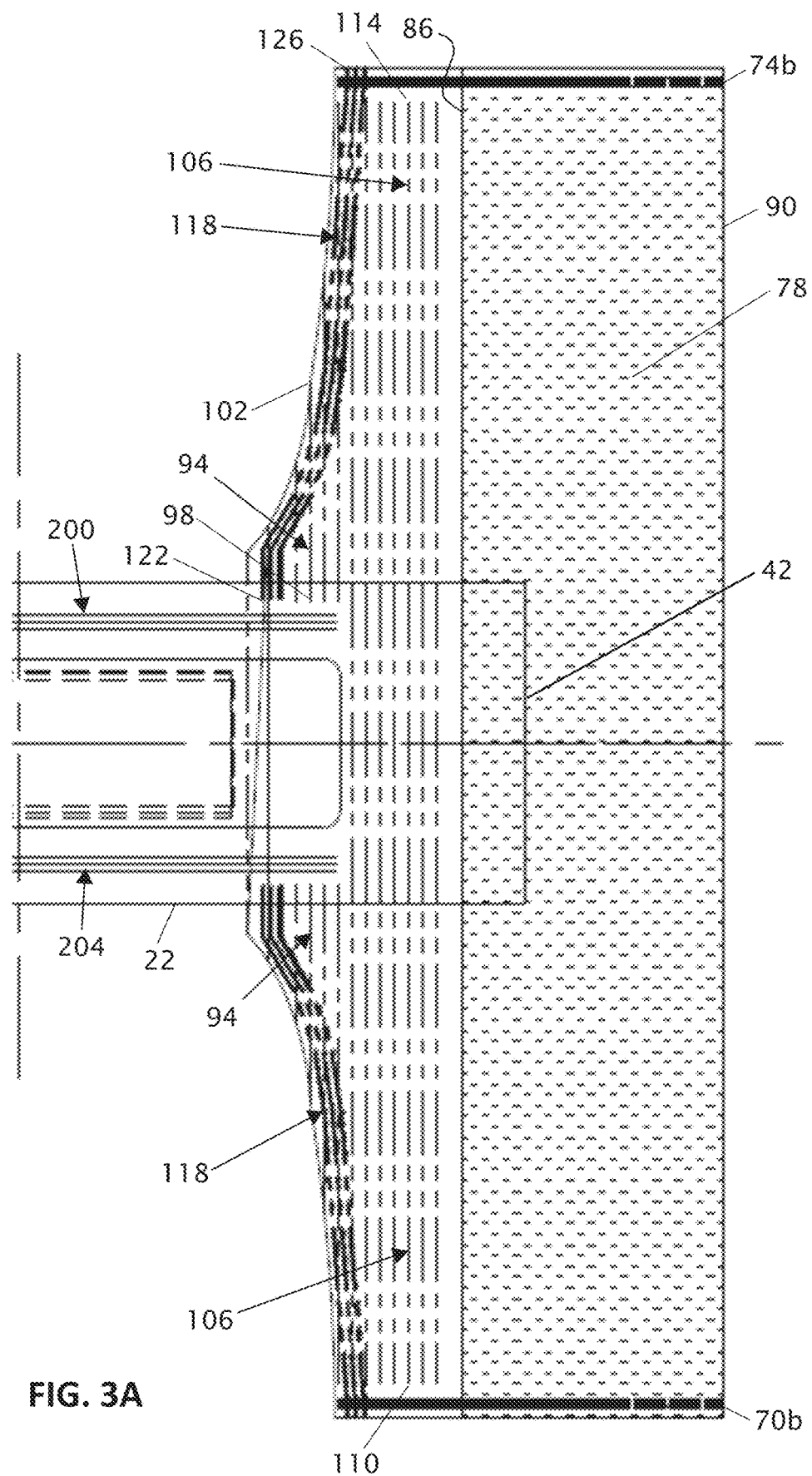
FIG. 3A depicts an enlarged, cutaway plan view of the front half of the garment of FIG. 1.
Figure 3B:
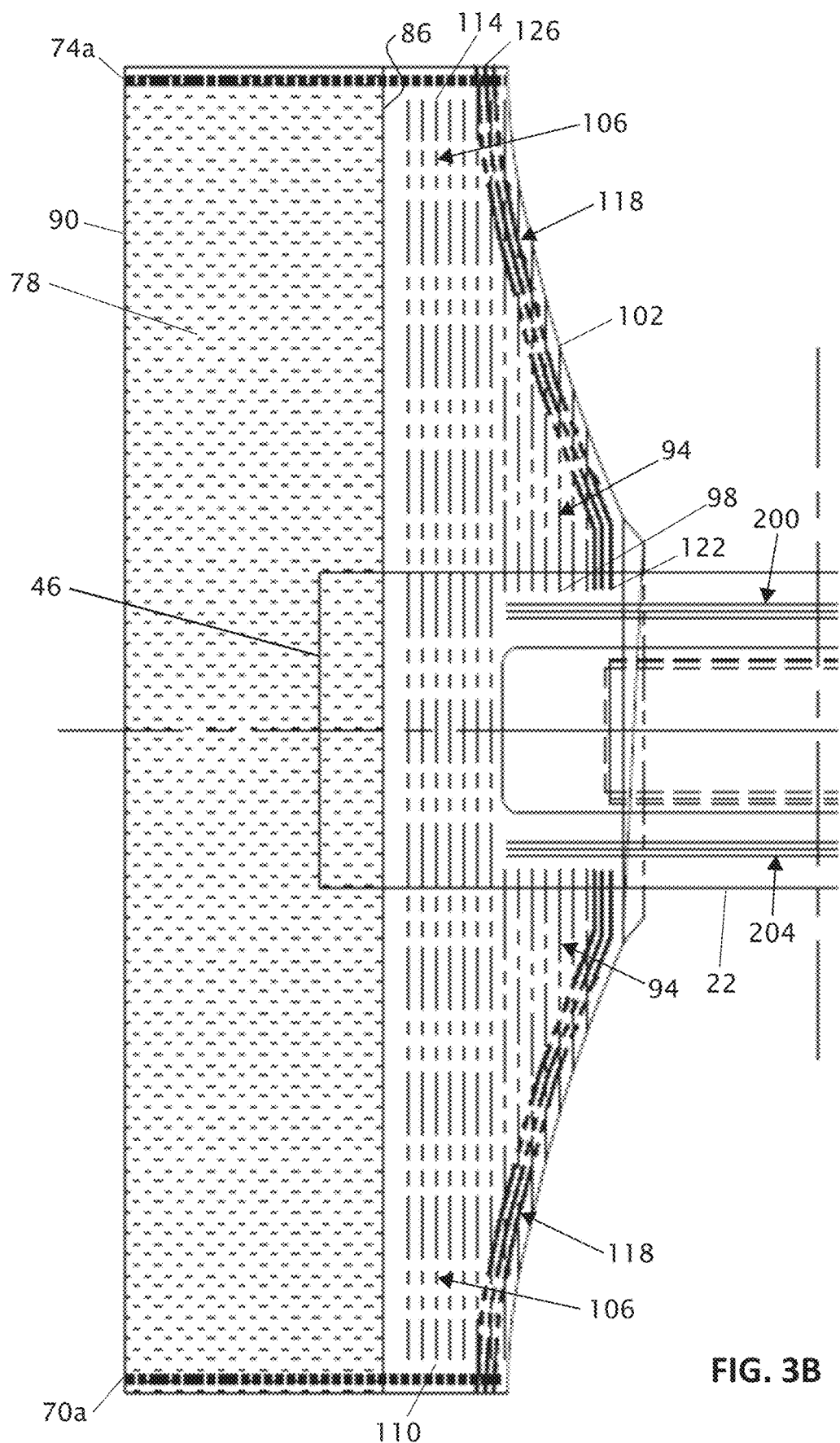
FIG. 3B depicts an enlarged, cutaway plan view of the rear half of the garment of FIG. 1.

Referring now to the drawings, and more particularly to FIGS. 1-3B, shown therein and designated with the reference numeral 10 is an embodiment of the present disposable absorbent garments. In the embodiment shown, garment 10 is comprises a front waist portion 14, a rear waist portion 18, and a central absorbent assembly 22. In this embodiment, front and rear waist portions each comprise a waist edge 26, a leg edge 30, and first and second side edges 34, 38 extending between waist edge 26 and leg edge 30. In the embodiment shown, central absorbent assembly 22 has a first end 42, a second end 46, and first and second leg edges 50, 54 extending between first and second ends 42, 46. In this embodiment, central absorbent assembly 22 comprises a liquid-absorbent core 58 and is coupled to front and rear waist portions 14, 18 such that the central absorbent assembly extends between the respective leg edges 30 of the front and rear waist portions.

As shown, in the depicted embodiment, the respective leg edges 30 of front and rear waist portions 14, 18 each include a central crotch portion 62 that is substantially parallel to the corresponding waist edge 26, and two lateral leg opening portions 66 that curve upward and outward toward the nearest side edge 34 or 38. This shape is configured to define, when the corresponding side edges of front and rear waist portions 14, 18 are joined, a pant-like or brief-like configuration (e.g., underpants) that is wearable by a user. More particularly, first side edge 34 of front waist portion 14 may be coupled to first side edge 34 of rear waist portion 18, and second side edge 38 of front waist portion 14 can be coupled to second side edge 38 of rear waist portion 18, such that central absorbent assembly 22 and front and rear waist portions 14, 18 together define a pair of leg openings each configured to receive a leg of a wearer, while the front and rear waist portions encircle the wearer's waist. In this embodiment, first side edge 30 of front waist portion 14 is configured to be coupled to first side edge 30 of rear waist portion 18 at a first tearable side seam 70, and second side edge 34 of front portion 14 is coupled to second side edge 38 of rear waist portion 18 at a second tearable side seam 74. Side seams 70 and 74 may, for example, comprise hook-and-loop fasteners (e.g., hook fasteners 70a, 74a and loop fasteners 70b, 74b), or may be adhesively, ultrasonically, or otherwise joined in a way that the seam may be separated by hand. The side seams of this embodiment are therefore configured to facilitate removal of garment 10 from a wearer by detaching the respective first side edges 34 of the front and rear waist portions and/or the respective second side edges 38 of the front and rear waist portions.

In some embodiments, at least one of the front and rear waist portions (14, 18) includes a composite of elastic sheet material and a non-woven fabric layer that also includes a plurality of elastic strands. For example, in the embodiment shown, front waist portion 14 comprises: an elastic sheet material 78 and a non-woven fabric layer 82. In the embodiment shown, elastic sheet material 78 and non-woven fabric layer are ultrasonically bonded to each other. In the depicted embodiment, elastic sheet material 78 extends from a first edge 86 that overlaps end 42 of central absorbent assembly 22, and extends toward waist edge 26 of the front waist portion to a second edge 90. In this embodiment, second edge 90 of elastic sheet material 78 extends to the corresponding waist edge 26. In other embodiments, the second edge (90) of the elastic sheet material may be offset or spaced from waist edge 26, and some such embodiments may comprise a plurality of waist elastic elements (not shown but, for example, including elastic strands) positioned between the waist edge 26 and the second edge (90) of the elastic sheet material (78). In some such embodiments, the waist elastic elements are positioned within an overturned portion (304 (FIG. 2B)) of the non-woven layer 82.

In the embodiment shown, front waist portion 14 also includes a first plurality of elastic strands 94 on both sides of core 58. Strands 94 may, for example, be spaced at intervals of less than 10 mm, between 4 mm and 8 mm, or substantially equal to 6 mm. In this embodiment, each of strands 94 has a first end 98 laterally offset from core 58 and extending outward toward a respective leg edge 30 of the waist portion to a second end 102 that is nearer to the leg edge (30) than the first end (98). For example, in the embodiment shown, each second end 102 terminates at the corresponding leg opening portion (66) of leg edge 30. In this embodiment, first ends 98 overlap a portion of central absorbent assembly 22 (i.e., a portion adjoining leg side 50 or leg side 54 of the central absorbent assembly), but do not overlap the absorbent core.

In the embodiment shown, front waist portion 14 further comprises a second plurality of elastic strands 106 between a corresponding end of the absorbent core (58) and elastic sheet material 78. Strands 106 may, for example, be spaced at intervals of less than 10 mm, between 4 mm and 8 mm, or substantially equal to 6 mm. In this embodiment, each of strands 106 extends laterally across a majority of front waist portion 14 between first and second side edges 34, 38 from a first end 110 to a second end 114. In this embodiment, ends 110 and 114 of strands 106 are disposed laterally inward of side seams 70 and 74 such that strands 106 do not overlap the tearable side seams. In other embodiments, strands 106 may overlap the tearable side seams. For example, in this embodiment, elastic sheet material 78 does overlap tearable side seams 70, 74 (e.g., extends laterally to side edges 34, 38 of front waist portion).

In the embodiment shown, front waist portion 34 also includes a third plurality of elastic strands 118 extending along leg opening portions 66 of leg edge 30. Strands 106 may, for example, be spaced at intervals of less than 10 mm, between 4 mm and 8 mm, or substantially equal to 6 mm. As shown, in this embodiment, each of strands 118 has a first end 122 laterally offset from core 58 and extends outward along a respective leg opening portion 66 of the leg edge (30) and toward a respective side edge 34, 38 of the waist portion to a second end 126. In this embodiment, strands 118 cross the respective side seam 70 or 74 such that second ends 126 terminate at the corresponding side edge 34 or 38. In other embodiments, second ends 126 may be laterally offset from (inward of) side seams 70, 74. In the depicted embodiment, first ends 122 of strands 118 overlaps a portion of central absorbent assembly 22 (i.e., a portion adjoining leg side 50 or leg side 54 of the central absorbent assembly), but do not overlap the absorbent core.

Referring now particularly to FIGS. 2A and 2B, the depicted example of the central absorbent assembly is shown in more detail. In this embodiment, central absorbent assembly 22 includes a first leg elastic element 200 and a second leg elastic element 204. As shown, first leg elastic element 200 extends between first leg edge 50 and core 58 (e.g., parallel to a portion of first leg edge 50), and second leg elastic element 204 extends between second leg edge 54 and core 58 (e.g., parallel to a portion of second leg edge 54). In this embodiment, a portion (e.g., end) of first leg elastic element 200 is disposed between a first portion of elastic strands 94 and core 58, and second elastic leg element 204 is disposed between a second portion of elastic strands 94 and core 58. Similarly, in this embodiment, a portion (e.g., end) of first leg elastic element 200 is disposed between a first portion of elastic strands 118 and core 58, and second elastic leg element 204 is disposed between a second portion of elastic strands 118 and core 58. In the embodiment, shown first and second leg elastic elements 200, 204 each comprise a plurality of (e.g., 3, as shown) elastic strands. Other embodiments may include 1, 2, 4, 5, or more elastic strands spaced at intervals of less than 10 mm, between 4 mm and 8 mm, or substantially equal to 6 mm. In other embodiments, leg elastic elements can comprise elastic film or other types of elastication elements.

In the embodiment shown, central absorbent assembly 22 also includes a liquid-permeable facing layer 208, and a substantially liquid-impermeable backing layer 212, with liquid-absorbent core 58 positioned between facing layer 208 and backing layer 212. In this embodiment, a liquid-acquisition layer 216 is also positioned between facing layer 208 and core 58. In some embodiments, such as the one shown, central absorbent assembly 22 can also include a liquid-absorbent surge layer 220 positioned between acquisition layer 216 and core 58. Such a surge layer can be configured to receive liquid that passes through facing layer 208 and acquisition layer 216, and transfer the received liquid into core 58 for absorption and retention.

In the embodiment shown, each of front and rear waist portions 14 and 18 comprise a backsheet 300 (e.g., nonwoven fabric layer) disposed below or outward (relative to a patient during use) of the composite of nonwoven fabric layer 78 and elastic sheet material 82, as shown. In the embodiment shown, a folded or overturned portion 304 defines waist edge 26. For example, in the embodiment shown, backsheet 300 is folded or overturned over end 90 of elastic sheet material 82 and the corresponding edge of nonwoven fabric layer 78. In other embodiments, elastic sheet material 82 may stop short of overturned portion 304 and waist elastic elements such as elastic strands may be disposed in overturned portion 304 (e.g., elastic strands spaced at intervals smaller than 10 millimeters (mm), between 2 mm and 6 mm, or substantially equal to 4 mm). Some embodiments omit overturned portion 304 entirely, but may still include elastic sheet material extending to the waist edge (26) or waist elastic elements between the elastic sheet material and the waist edge (26).

In this embodiment, backsheet 300 includes two separate pieces each spanning only one of front waist portion 14 and rear waist portion 18, and backing layer 212 functions as the sole backsheet for central absorbent portion. In other embodiments, such as those with a single-piece construction, backsheet 300 includes a single piece of material that spans front waist portion 14, rear waist portion 18, and central absorbent assembly 22; in such embodiments, nonwoven layer 82 can also include a single piece of material that spans front waist portion 14, rear waist portion 18, and central absorbent assembly 22.

While the foregoing has particularly described front waist portion 14, and as is be apparent from the figures, rear waist portion 18 is substantially similar to front waist portion 14 with respect to the features described. For example, rear waist portion 18 includes the same basic elements in a very similar configuration that differs only in the number of certain elastic strands (94 and 106) and the particular profile of leg opening portions 66 of leg edge 30. In other embodiments, front and rear waist portions 14 and 18 may not be substantially similar. For example, one of the front waist portion (14) or the rear waist portion (18) may (i) not include the present hybrid elastic composite of film and elastic strands, or (ii) may omit strands 94 or strands 106 (e.g., in favor of additional elastic film or other elastication elements).

The present hybrid-elastic embodiments are configured to enhance user fit and comfort via the inclusion, in one or both of the front and rear waist portions, both elastic film and elastic strands (e.g., elastic strands that laterally span a majority of the width of the respective waist portion, and/or elastic strands that span only a portion of the width of the waist portion between the liquid-absorbent core and a respective leg edge.

From the foregoing, it will be observed that numerous modifications and variations can be effected without departing from the true spirit and scope of the novel concept of the present invention. It is to be understood that no limitation with respect to the specific embodiments disclosed herein is intended or should be inferred. The disclosure is intended to cover, by the appended claims, all such modifications as fall within the scope of the claims.

The invention claimed is:

1. A disposable absorbent garment, comprising:
front and rear waist portions each having a waist edge, a leg edge, and first and second side edges extending between the waist edge and the leg edge; and
a central absorbent assembly having a first end, a second end, and first and second leg edges extending between the first and second ends, the central absorbent assembly coupled to the front and rear waist portions such that the central absorbent assembly extends between the respective leg edges of the front and rear waist portions, the central absorbent assembly comprising a liquid-permeable facing layer, a substantially liquid-impermeable backing layer, and a liquid-absorbent core positioned between the facing layer and the backing layer;
where at least one of the front and rear waist portions comprises:
a composite of an elastic sheet material and a nonwoven fabric layer, the elastic sheet material overlapping a respective end of the central absorbent assembly and extending toward the waist edge of the waist portion;
a first plurality of elastic strands on both sides of the liquid-absorbent core, each of the first plurality of elastic strands having a first end laterally offset from the liquid-absorbent core and extending outward toward a respective leg edge of the waist portion, the leg edge different from the first and second side edges, where the first plurality of elastic strands do not extend across an entirety of the central absorbent assembly; and
a second plurality of elastic strands between the liquid-absorbent core and the elastic sheet material, each of the second plurality of elastic strands extending laterally across a majority of the waist portion between the first and second side edges, and the second plurality of elastic strands being substantially parallel to the first plurality of elastic strands.

2. The disposable absorbent garment of claim 1, where the at least one of the front and rear waist portions further comprises:
a third plurality of elastic strands each having a first end laterally offset from the liquid-absorbent core and extending outward along a respective leg edge and toward a respective side edge of the waist portion; and
where the first plurality of elastic strands, the second plurality of elastic strands, and the third plurality of elastic strands are included in the same waist portion of the front and rear waist portions.

3. The disposable absorbent garment of claim 2, where the first end of each of the third plurality of elastic strands overlaps a portion of the central absorbent assembly.

4. The disposable absorbent garment of claim 1, where the first end of each of the first plurality of elastic strands overlaps a portion of the central absorbent assembly.

5. The disposable absorbent garment of claim 4, where the central absorbent assembly further comprises:
a first leg elastic element extending parallel to a portion of the first leg edge between the first leg edge and the liquid-absorbent core; and
a second leg elastic element extending parallel to a portion of the second leg edge between the second leg edge and the liquid-absorbent core.

6. The disposable absorbent garment of claim 5, where the first leg elastic element is disposed between a first portion of the first plurality of elastic strands and the liquid-absorbent core, and the second elastic leg element is disposed between a second portion of the first plurality of elastic strands and the liquid-absorbent core.

7. The disposable absorbent garment of claim 6, where the first leg elastic element comprises a plurality of elastic strands, and the second leg elastic element comprises a plurality of elastic strands.

8. The disposable absorbent garment of claim 5, where the central absorbent assembly further comprises:
a liquid-acquisition layer positioned between the facing layer and the liquid-absorbent core.

9. The disposable absorbent garment of claim 8, where the central absorbent assembly further comprises:
a liquid-absorbent surge layer positioned between the acquisition layer and the liquid-absorbent core, the liquid-absorbent surge layer configured to receive liquid that passes through the facing layer and the acquisition layer, and transfer the received liquid into the liquid-absorbent core.

10. The disposable absorbent garment of claim 1, where the first side edge of the front waist portion is coupled to the first side edge of the rear waist portion, and the second side edge of the front waist portion is coupled to the second side edge of the rear waist portion, such that the central absorbent assembly and the front and rear waist portions together define a pair of leg openings each configured to receive a leg of a wearer.

11. The disposable absorbent garment of claim 10, where the first side edge of the front waist portion is coupled to the first side edge of the rear waist portion at a first tearable side seam, the second side edge of the front waist portion is coupled to the second side edge of the rear waist portion at a second tearable side seam, and the first and second tearable side seams are configured to facilitate removal of the disposable absorbent garment from a wearer by detaching the respective first side edges of the front and rear waist portions, the respective second side edges of the front and rear waist portions, or the first and second side edges of the front and rear waist portions.

12. The disposable absorbent garment of claim 1, where, in the at least one of the front and rear waist portions, the elastic sheet material extends to the waist edge of the waist portion.

13. The disposable absorbent garment of claim 1, where the at least one of the front and rear waist portions comprises a plurality of waist elastic elements positioned between the waist edge and the elastic sheet material.

14. The disposable absorbent garment of claim 13, where the plurality of waist elastic elements are positioned within an overturned portion of the non-woven fabric layer.

15. The disposable absorbent garment of claim 1, where the front waist portion is substantially similar to the rear waist portion.

16. A disposable absorbent garment, comprising:
front and rear waist portions each having a waist edge, a leg edge, and first and second side edges extending between the waist edge and the leg edge;
a central absorbent assembly having a first end, a second end, and first and second leg edges extending between the first and second ends, the central absorbent assembly coupled to the front and rear waist portions such that the central absorbent assembly extends between the respective leg edges of the front and rear waist portions, the central absorbent assembly comprising a liquid-permeable facing layer, a substantially liquid-impermeable backing layer, and a liquid-absorbent core positioned between the facing layer and the backing layer;
where at least one of the front and rear waist portions comprises:
a composite of an elastic sheet material and a non-woven fabric layer, the elastic sheet material overlapping a respective end of the central absorbent assembly and extending toward the waist edge of the waist portion;
a first plurality of elastic strands between the liquid-absorbent core and the elastic sheet material, each of the first plurality of elastic strands having a first end laterally offset from the liquid-absorbent core and extending outward toward a respective leg edge of the waist portion, the leg edge different from the first and second side edges, where the first plurality of elastic strands do not extend across an entirety of the central absorbent assembly; and
a second plurality of elastic strands each having a first end laterally offset from the liquid-absorbent core and extending outward along a respective leg edge and toward a respective side edge of the waist portion, and the second plurality of elastic strands being substantially parallel to the first plurality of elastic strands.

17. The disposable absorbent garment of claim 16, where the first side edge of the front waist portion is coupled to the first side edge of the rear waist portion at a first tearable side seam, and the second side edge of the front portion is coupled to the second side edge of the rear waist portion at a second tearable side seam.

18. The disposable absorbent garment of claim 17, where the first plurality of elastic strands do not overlap the tearable side seams.

19. The disposable absorbent garment of claim 1, where the first plurality of elastic strands are substantially parallel to the waist edge of the respective waist portion.

* * * * *